United States Patent [19]

Becker et al.

[11] 3,944,620

[45] Mar. 16, 1976

[54] PROCESS FOR THE PREPARATION OF OXOPHORONES

[75] Inventors: Joseph J. Becker; Ulrich P. Hochstrasser; Werner Skorianetz, all of Geneva, Switzerland

[73] Assignee: Firmenich S.A., Geneva, Switzerland

[22] Filed: Nov. 26, 1974

[21] Appl. No.: 527,449

[30] Foreign Application Priority Data

July 10, 1974   Switzerland.......................... 9479/74

[52] U.S. Cl.............................................. 260/586 P
[51] Int. Cl.² .................... C07C 45/00; C07C 45/04
[58] Field of Search................................. 260/586 P

[56] References Cited

UNITED STATES PATENTS

| | | | |
|---|---|---|---|
| 2,819,298 | 1/1958 | Isler et al. | 260/586 P |
| 2,917,539 | 12/1959 | Isler et al. | 260/586 P |
| 3,070,629 | 12/1962 | Ohloff et al. | 260/586 P |
| 3,404,185 | 10/1968 | Thomas et al. | 260/586 P |

FOREIGN PATENTS OR APPLICATIONS 1,066,709   9/1965   United Kingdom ............ 260/586 P

*Primary Examiner*—Norman Morgenstern
*Attorney, Agent, or Firm*—Pennie & Edmonds

[57] ABSTRACT

Process for the preparation of a diketone derivative, viz 2,2,6-trimethyl-cyclohex-5-en-1,4-dione, an organoleptically interesting ingredient for the perfumery and the flavour industry, as well as a useful intermediate for the pharmaceutical industry.

4 Claims, No Drawings

PROCESS FOR THE PREPARATION OF OXOPHORONES

BACKGROUND OF THE INVENTION

Owing to its intrinsic organoleptic properties and to its particular chemical structure, 2,2,6-trimethylcyclohex-5-en-1,4-dione (hereinafter referred to as oxophorone) has focused the attention of several research groups over the past. Namely, its synthesis has been thoroughly investigated and described in the scientific literature as well as in various patent specifications [see e.g.: Tetrahedron Suppl., 8, 1–7 (1966): Helv. Chim. Acta, 39, 2041 (1956) and U.S. Pat. No. 2,917,539].

However, the synthetic routes known sofar suffer from the disadvantages of producing low yields of the desired diketone, or comprising several successive reaction steps, and of requiring the use of relatively expensive reagents, so that they are unsuitable for use on an industrial scale.

THE INVENTION

The present invention provides a novel process for the preparation of oxophorone, said process comprising an oxidation of 3,5,5-trimethyl-cyclohex-2-en-1-one (hereinafter referred to as isophorone), in the liquid phase, by means of oxygen, or an oxygen containing gas mixture in the presence of a metal catalyst selected from the group consisting of a salt, an oxide and an organic derivative of a d block metal.

Such a process offers the advantage of using as starting material a commercial compound readily available at low price and promoting its more complete conversion into oxophorone. Its subsequent purification is thus made easier. By making use of a one step synthesis, the process of the invention is economical and industrially advantageous.

PREFERRED EMBODIMENTS OF THE INVENTION

According to the process of this invention the oxidizing reagent is pure oxygen or an oxygen containing gas mixture wherein oxygen is in admixture with an inert gas such as nitrogen, helium or argon. Whenever an oxygen containing gas mixture is used, the proportions of oxygen in the mixture can vary within a wide range. For economical and practical reasons however, air is used. In such a case, though slower, the oxidation reaction proceeds in a more controlled manner than by the use of pure oxygen and the formation of tarry residues is rendered negligible. The reaction time depends on a variety of factors and is namely a function of the oxygen content of the oxidizing gas mixture, a higher oxygen content generally promoting a faster reaction.

In accordance with a preferred embodiment of this invention, the oxidation of isophorone is performed in a reaction vessel equipped with a highly efficient stirrer. It has been observed in fact that the best yields of oxophorone were achieved by promoting a regular and homogeneous distribution of the gas stream throughout the whole mass of the material subjected to oxidation. This gas stream could be introduced by means of a compressor or by means of a self-initiating turbine. It has to be understood however that all devices able to promote such a uniform distribution of the gas mixture, e.g. a sintered glass funnel, can be used instead.

The gas flow can also vary within wide limits and depends on the volume of starting material used, the reactors size and the desired reaction time. In the example given hereinafter, certain values are indicated, but it is to be understood that they must not be construed restrictively.

The reaction temperatures are preferentially comprised between about 80° and 180°C. At a temperature higher than the above given upper limit, the reaction was particularly short but the direct oxidation reaction was accompanied by the concomitant formation of more or less important amounts of tarry residues. At temperatures lower than 80°C instead, the course of the oxidation was easily controlled but the reaction time was too long. Preferential temperatures are of from about 100° to 130°C, more preferably of about 110°–120°C.

Suitable oxidation catalysts include a salt, an oxide and an organic derivative of a d block metal [for a definition of a d block metal see e.g.: F. A. Cotton and G. Wilkinson, Advanced Inorganic Chemistry, Interscience Publishers, III Ed., p. 528 and ff.]. An organic derivative of vanadium, chromium, manganese, iron, cobalt, copper, nickel or rhodium can advantageously be used.

In accordance with a preferred embodiment of the process of the invention, vanadium$^{III}$-acetylacetonate, iron$^{III}$-acetylacetonate, cobalt$^{III}$-acetylacetonate or a rhodium$^{I}$ derivative such as tris-triphenylphosphine-rhodium chloride, can be used.

The proportions of oxidation catalyst relative to starting isophorone can vary within a wide range. Typically, they are of from about 0.3 to 10 % by weight, preferentially of about 0.5 %. Said catalyst can be added to the reaction mixture in the lump at the beginning of the reaction or by small portions in the course of the reaction. In this latter case the catalyst can be added, if desired by means of a delivery pump, in solution or in suspension in a small amount of isophorone, which method is particularly suitable for treating large quantities of starting material.

By the process of the invention the achieved yields of oxophorone are of about 30 to 40 % by weight, the balance being almost exclusively constituted by unreacted isophorone. This latter can be easily recovered from the reaction mixture by simple fractional distillation and subjected anew to the oxidation process.

Though the oxidation reaction occurs with best yields in the presence of an oxidation catalyst, it has been observed that said reaction may also occur in the absence of such a catalyst. Direct oxidation of isophorone by means of oxygen, or an oxygen containing gas mixture, provided in fact oxophorone with yields ranging from about 18 to 22 % by weight.

It is reasonable to assume that the oxidation reaction which characterizes the process of the invention occurs, at least partially, on the isomerized form of isophorone, i.e. via the transient formation of β-phorone, according to the following reaction scheme:

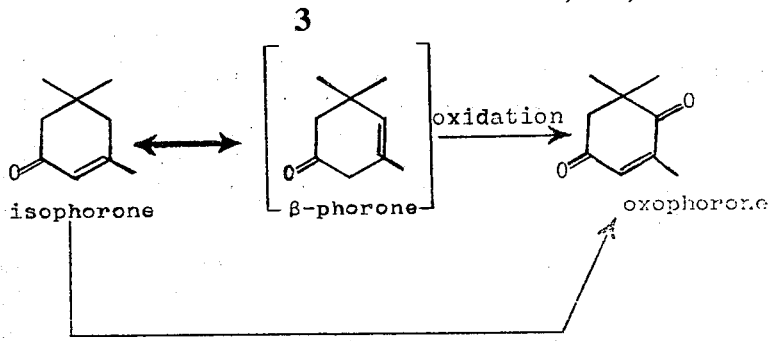

The invention will be illustrated but not limited by the following example, wherein the temperatures are indicated in degrees centigrade and the abbreviations have the meaning usual in the art.

EXAMPLE 350 g of isophorone were heated to 130° and kept to this temperature under vigourous stirring in a reaction vessel equipped with a condenser and a self-initiating turbine. Air was thus introduced at an initial flow rate of 100–150 l/h. The flow was then increased progressively up to 300 l/h and 3.5 g of vanadium$^{III}$-acetylacetonate (Wacker Chemie GmbH, Munich) were added to the reaction mixture. 3.5 g samples of vanadium$^{III}$-acetylacetonate were added after 21, 28, 45 and 53 hours. The mixture was further stirred for 15 h at 130°, whereupon 224 g of a fraction having b.p. 80°–98°/12 Torr were collected by fractional distillation. This fraction contained 36 % by weight of oxophorone and 64 % by weight of starting isophorone, as indicated by a vpc analysis on a CARBOWAX 20 M column of 2.7 m length at a programmed temperature of 140° to 200°.

Pure oxophorone was isolated by fractional distilling the obtained mixture. The fraction boiling at 95°–96°/12 Torr was in all respects identical to a sample obtained in accordance with the procedure described in Helv. Chim. Acta, 39, 2041 (1956).

A set of experiments was carried out by following the same procedure as that given in the above example and varying the following parameters:
reaction temperature
oxidizing gas mixture
catalyst and proportions thereof
addition procedure
reaction time.
The results achieved and the reaction conditions used are summarized in the hereinbelow given Table. The proportions indicated of the various reagents are expressed relative to 100 g of starting isophorone. The abbreviations and the signs stated have the meaning given hereinbelow:

A = vanadium$^{III}$-acetylacetonate;
B = rhodium$^{I}$-tris-triphenylphosphine chloride;
C = iron$^{III}$-acetylacetonate;
D = no catalyst;
E = cobalt$^{III}$-acetylacetonate;
+ = addition of 4 equal portions at regular intervals;
o = addition in the lump at the beginning of the reaction.

TABLE

| Experiment | Type | Catalyst Quantity [g] | Catalyst Addition | Oxidizing gas mixture | Temp. [°C] | Time [h] | Distillate 80–98°/12 Torr Quantity [g] | % oxophorone |
|---|---|---|---|---|---|---|---|---|
| 1 | A | 12 | + | air | 113 | 45 | 51 | 29 |
| 2 | A | 6 | + | air | 120 | 85 | 63 | 35 |
| 3 | A | 5 | o | air | 110 | 41 | 76 | 13 |
| 4 | A | 1.8 | + | O$_2$ | 115 | 50 | 57 | 40 |
| 5 | B | 1 | o | air | 110 | 56 | 56 | 31 |
| 6 | C | 1.3 | + | O$_2$ | 110 | 44 | 58 | 34 |
| 7 | A | 0.6 | + | O$_2$ | 112 | 66 | 58 | 40 |
| 8 | A | 0.6 | + | air | 110 | 50 | 85 | 26 |
| 9 | A | 0.6 | + | O$_2$ | 95 | 41 | 54 | 27 |
| 10 | D | — | — | air | 120 | 100 | — | 20 |
| 11 | D | — | — | air | 139 | 100 | — | 21.4 |
| 12 | E | 2.1 | + | air | 70 | 34 | — | 35 |

What we claim is:

1. Process for the preparation of 2,2,6-trimethyl-cyclohex-5-en-1,4-dione, which comprises oxidizing 3,5,5-trimethyl-cyclohex-2-en-1-one, in the liquid phase, by means of oxygen, or an oxygen containing gas mixture in the presence of a metal catalyst selected from a salt or an oxide of vanadium, chromium, manganese, iron, cobalt, nickel or rhodium or an organic derivative of vanadium, iron, cobalt or rhodium at a temperature of from about 80° to 180°C.

2. Process according to claim 1, wherein the catalyst is selected from the group consisting of vanadium$^{III}$-acetylacetonate, iron$^{III}$-acetylacetonate, cobalt$^{III}$-acetylacetonate, and rhodium$^{I}$-tris-triphenylphosphine chloride.

3. Process according to claim 1, wherein the oxidation is carried out at a temperature of from about 100° to 130°C.

4. Process according to claim 1, wherein the oxidation is performed by means of air or oxygen enriched air.

* * * * *